United States Patent [19]

Wellstein

[11] Patent Number: 5,789,382
[45] Date of Patent: Aug. 4, 1998

[54] RETRO-PEPTIDE FIBROBLAST GROWTH FACTOR WHICH BLOCKS FGF RECEPTOR

[75] Inventor: Anton Wellstein, Washington, D.C.

[73] Assignee: Georgetown University, Washington, D.C.

[21] Appl. No.: 133,271

[22] Filed: Oct. 7, 1993

Related U.S. Application Data

[63] Continuation of Ser. No. 651,601, Feb. 6, 1991, abandoned.

[51] Int. Cl.$^6$ .............. A61K 38/10; C07K 7/08; C07K 14/71
[52] U.S. Cl. .............. 514/14; 424/400; 530/326
[58] Field of Search .............. 530/326, 399; 930/31; 514/12–14; 424/400

[56] References Cited

U.S. PATENT DOCUMENTS

| | | | |
|---|---|---|---|
| 4,360,516 | 11/1982 | Freidinger | 424/177 |
| 5,132,408 | 7/1992 | Baird | 530/399 |
| 5,192,746 | 3/1993 | Lobl | 514/11 |
| 5,252,718 | 10/1993 | Baird | 530/399 |

FOREIGN PATENT DOCUMENTS 0375040   6/1990   European Pat. Off. .

OTHER PUBLICATIONS

J. Kyte & R.F. Doolittle J. Mol. Biol. 157:105–132 1982.
P. Guptasarma FEBS Lett. 310(3):205–210 Oct. 1992.
CF Hayward & J.S. Morley Eur. Peptide Symp. 13:28798 Apr. 1974.
A. Baird et al. PNAS 85:2324–2328 1988.
A. Ricouart et al. Biochem Biophys Res Comm. 165(3) 1382–1390 1989.

*Primary Examiner*—Lorraine Spector
*Attorney, Agent, or Firm*—Oblon, Spivak, McClelland, Maier & Neustadt, P.C.

[57] ABSTRACT

A fibroblast growth factor receptor-blocking peptide is provided. In one embodiment, the peptide is a retro-peptide of the fibroblast growth factor receptor. The receptor-blocking peptide may be used in a therapeutic method for treatment of viral diseases, hypervascular diseases, and tumors.

4 Claims, 5 Drawing Sheets

```
:::: :
QKLAVYYYIIHRERR  100
UL21 protein - Herpes simplex virus (type 1, strain 17)

:::: :
QKLAVYYYIIHRERR  100
Hypothetical protein - Herpes simplex virus (type 1, strain HFEM)

::  ::::  :
GKLIPYWGSVKEDRI  110
Genome polyprotein - Japanese encephalitis virus (wild type, strain JaOArS982) (3432)
```

FIG. 5

RETRO-PEPTIDE FIBROBLAST GROWTH FACTOR WHICH BLOCKS FGF RECEPTOR

This application is a Continuation of application Ser. No. 07/651,601, filed on Feb. 6, 1991, now abandoned.

BACKGROUND OF THE INVENTION

1. Field of the Invention

The present invention relates to receptor blocking peptides of fibroblast growth factor receptor.

2. Description of the Background

It is known that cells can gain growth autonomy by acquiring the ability to produce, secrete and respond to a given growth factor. For example, in 1975, a peptide mitogen for 3T3 cells was extracted and purified from bovine pituitary tissue, and was named fibroblast growth factor (FGF) and subsequently characterized as a basic polypeptide exhibiting mitogenic activity for mesoderm- and neuroectoderm-derived cells. Somewhat later, an additional polypeptide mitogen for human endothethial cells was characterized from extracts of neural tissue and designated acidic FGF due to its acidic isoelectric point.

More recently, the molecular characterization of basic and acidic fibroblast growth factors has confirmed the existence of two classes of closely related angiogenic factors which help to establish the identity of a family of mitogens. Both acidic and basic fibroblast growth factors exist in several molecular forms which stimulate a wide spectrum of target cells derived from the primary and secondary mesenchyme as well as from the neural crest. Both fibroblast growth factors also have the capacity to stimulate neovascularization and their physiological functions have been associated with reproduction, growth and development.

However, it has been suggested that this family of mitogens may also play a critical role in several pathophysiological processes including the growth of tumors, diabetic proliferative retinopathies and the wound healing response. Folkman, J. *Ann Surg.* 175, 409–416 (1972).

Even more recently, it was discovered that the basic FGF receptor is used as a means of entry for Herpes Simplex virus type 1 (HSV-1). See Kaner, R. J. et al. *Science*, vol. 248, 1410–1412 (1990). In that study, it was found that Chinese hamster ovary (CHO) cells that do not express FGF receptors were resistant to HSV-1 entry, whereas CHO cells transfected with a complementary DNA encoding a basic FGF receptor, exhibited dramatically increased HSV-1 uptake. This paper concluded, however, that the mechanism by which the HSV-1 virion recognizes the basic FGF receptor was still undefined.

In a separate study, it was discovered that specific analogues of FGF are capable of inhibiting the biological effects of FGF with specificity. Baird, A. et al, *Proc. Natl. Acad. Sci.*, vol. 85, pp. 2324–2328 (1988). One such analog is the peptide sequence NH$_2$-YRSRK-YSSWY-VALKR-COOH (SEQ ID NO:1), i.e., the antero-peptide sequence. However, the inhibiting effects of the FGF analogues described therein are of limited potency.

Thus, it would be extremely advantageous if a blocking peptide could be obtained to block the effects of FGF at its receptor site with specificity and with increased potency.

SUMMARY OF THE INVENTION

Accordingly, it is an object of the present invention to provide a blocking peptide for FGF receptor.

It is also an object of the present invention to provide a therapeutic method for viral diseases, such as herpes; hypervascular diseases such as arthritis, psoriasis and cardiovascular deficiencies; and in the treatment of tumors.

The above objects and others which will be described hereinbelow are provided by a peptide of the formula:

wherein α is an amino acid having an R value of 4.5±1 unit; β is an amino acid having an R value of 3.9±1 unit; γ is an amino acid having an R value of −3.8±1 unit; δ is an amino acid having an R value of −1.8±1 unit; ε is an amino acid having an R value of −4.2±1 unit; η is an amino acid having an R value of −1.3±1 unit; θ is an amino acid having an R value of 0.9±1 unit; κ is an amino acid having an R value of 0.8±1 unit; λ is an amino acid having an R value of 0.8±1 unit; μ is an amino acid having an R value of −1.3±1 unit; π is an amino acid having an R value of 3.9±1 unit; and ρ is from 1 to about 18 amino acid residues having an average R value of at least about 0±1 unit; and wherein both α and the last residue of ρ comprise hydrophilic end groups; or α is from 1 to about 18 amino acid residues having an average R value of at least about 0±1 unit; β, γ, δ, ε, η, θ, κ, λ, μ and π are as defined above and ρ is an amino acid having an R value of −1.3±1 unit; and wherein both the first residue of α and ρ comprise hydrophilic end groups.

BRIEF DESCRIPTION OF THE DRAWINGS

FIG. 5 illustrates the significant sequence homologies of a retro-peptide of the present invention (SEQ ID NO:2) and the Herpes Simplex virus UL21 protein (SEQ ID NO:3) and the Japanese encephalitis virus genome polyprotein (SEQ ID NO:4).

DETAILED DESCRIPTION OF THE PREFERRED EMBODIMENTS

Figure 1:
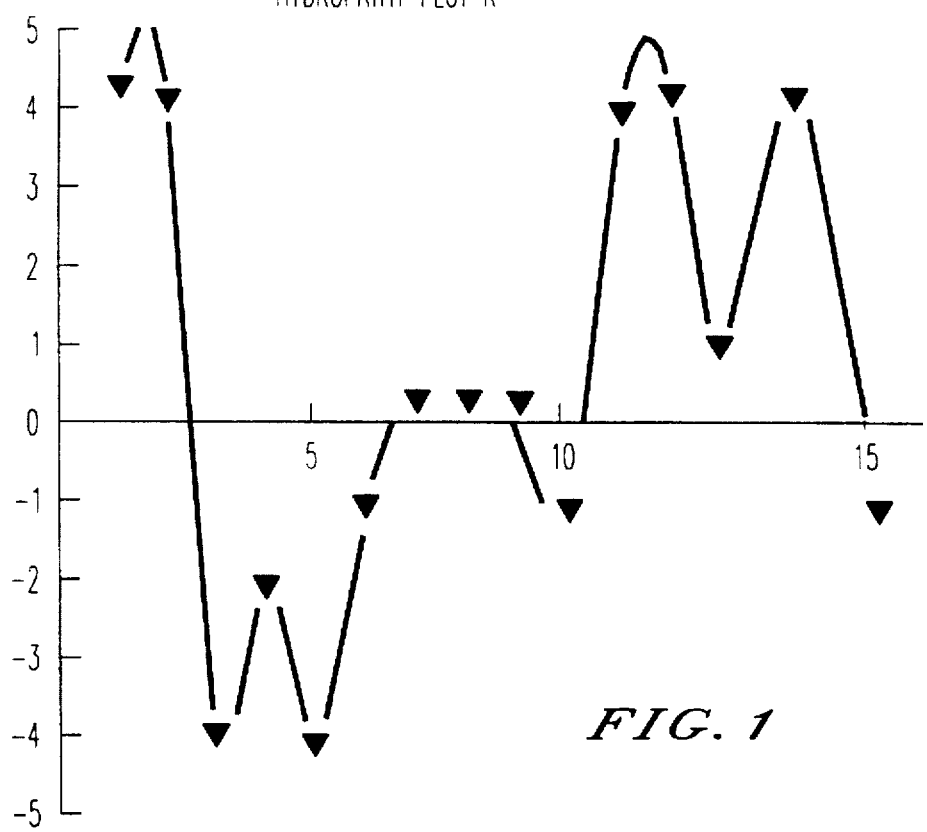
FIG. 1 illustrates the hydropathy pattern of a 15-mer peptide sequence of the present invention.

The present invention is based on the discovery that the physico-chemical properties of peptides are the main driving force for the recognition of a given receptor. By reversing a peptide sequence and making the C-terminal amino acid into the N-terminal amino acid, i.e., a retro-peptide, the mirror image peptide of a given peptide is formed and a completely new sequence is derived. This mirror image may be expected to have similar physico-chemical properties and surface structure as the antero-peptide. However, the new peptide, i.e., the retro-peptide, is a stereoisomer of the parent compound. The physico-chemical properties of the original recognition sequence remain the same. Thus, the new peptide is capable of recognizing the given receptor and occupying the same. However, the retro-peptide is unlikely to stimulate the receptor due to its novel stereo-configuration.

In accordance with the present invention, it has been discovered that certain peptide sequences are capable of functioning as potent FGF receptor blockers. Generally, these peptides have from about 12 to about 30 amino acid units, and necessarily have a hydrophilic amino acid residue at both sequence ends. Thus, two hydrophilic ends are required to conserve activity.

Further, the peptides of the present invention have the general formula:

$$NH_2-\alpha\beta\gamma\delta\epsilon\eta\theta\kappa\lambda\mu\pi-\rho-CO_2H$$

wherein α is an amino acid having an R value of 4.5±1 unit, β is an amino acid having an R value of 3.9±1 unit; γ is an amino acid having an R value of -3.8±1 unit, δ is an amino acid having an R value of -1.8±1 unit; ε is an amino acid having an R value of -4.2±1 unit; η is an amino acid having an R value of -1.3±1 unit; θ is an amino acid having an R value of 0.9±1 unit; κ is an amino acid having an R value of 0.8±1 unit; λ is an amino acid having an R value of 0.8±1 unit; μ is an amino acid having an R value of -1.3±1 unit; π is an amino acid having an R value of 3.9±1 unit; and ρ is from 1 to about 18 amino acid residues having an average R value of at least about 0±1 unit; and wherein both α and the last residue of ρ comprise hydrophilic end groups; or α is from 1 to about 18 amino acid residues having an average R value of at least about 0±1 unit; β, γ, δ, ε, η, θ, κ, λ, μ and π are as defined above and ρ is an amino acid having an R value of -1.3±1 unit; and wherein both the first residue of α and ρ comprise hydrophilic end groups.

The present peptides are defined, in essence, by the presence of two hydrophilic end groups, and having an internal sequence of amino acid residues, each having a particular range of R, or hydropathy, values. By the term "hydrophilic end groups" is meant that each end group must have an R value of 0±1, preferably about at least 0.5. The R value for the first residue of α and the last residue of q must meet this requirement. It is even more preferred, however, if each has an R value of at least about 1.0.

For purposes of the present invention, the R values of Kyte and Doolittle (*J. Mol. Biol.* 157: 105–132 (1982)) are used, and are reproduced hereinbelow for convenience. The standard one- and three-letter amino acid abbreviations are also provided.

In accordance with the present invention, it is specifically contemplated that any known and appropriate amino acid may be used, including non-natural amino acids or chemical replacements for amino acids, as long as the R value requirements described above are satisfied for the various sequential positions.

In accordance with the present invention, it has been discovered that the Herpes Simplex virus contains a protein having a sequence which is quite homologous to the present retro-peptide sequences. In fact, several viral envelope proteins have significant sequence homology to the present retro-peptides.

TABLE 1

| (R) Amino Acid | Single letter code | Triple letter code | Hydropathy value |
|---|---|---|---|
| Alanine | A | Ala | -1.8 |
| Arginine | R | Arg | 4.5 |
| Asparagine | N | Asn | 3.5 |
| Aspartic Acid | D | Asp | 3.5 |
| Cysteine | C | Cys | -2.5 |
| Glutamic Acid | E | Glu | 3.5 |
| Glutamine | Q | Gln | 3.5 |
| Glycine | G | Gly | 0.4 |
| Histidine | H | His | 3.2 |
| Isoleucine | I | Ile | -4.5 |
| Leucine | L | Leu | -3.8 |
| Lysine | K | Lys | 3.9 |
| Methionine | M | Met | -1.9 |
| Phenylalanine | F | Phe | -2.8 |
| Proline | P | Pro | 1.6 |
| Serine | S | Ser | 0.8 |
| Threonine | T | Thr | 0.7 |
| Tryptophan | W | Trp | 0.9 |
| Tyrosine | Y | Tyr | -1.3 |
| Valine | V | Val | -4.2 |

Of particular interest, in accordance with the present invention are peptide sequences of the formula:

$$NH_2-\alpha-\beta\gamma\delta\epsilon\eta\theta\kappa\lambda\mu\pi-\rho-CO_2H$$

wherein:

α is arginine (R:4.5), asparagine (R:3.5), aspartic acid (R:3.5), glutamic acid (R:3.5), glutamine (R:3.5) and lysine (R:3.9);

β is arginine (R:4.5), asparagine (R:3.5), aspartic acid (R:3.5), glutamic acid (R:3.5), glutamine (R:3.5), histidine (R:3.2) and lysine (R:3.9);

γ is isoleucine (R:-4.5), leucine (R:-3.8), phenylalanine (R:-2.8) and valine (R:-4.2);

δ is alanine (R:-1.8), cysteine (R:-2.5), glycine (R:0.4), methionine (R:-1.9), phenylalanine (R:-2.8), serine (R:0.8), threonine (R:0.7) and tyrosine (R:-1.3);

ε is isoleucine (R:-4.5), leucine (R:-3.8) and valine (R:-4.2);

η is alanine (R:-1.8), phenylalanine (R:-1.9) and tyrosine (R:-1.3);

θ is glycine (R:0.4), proline (R:1.6), serine(R:0.8), threonine (R:0.7) and tryptophan (R:0.9);

κ is glycine (R:0.4), proline (R:1.6), serine (R:0.8), threonine (R:0.7) and tryptophan (R:0.9);

λ is glycine (R:0.4), proline (R:1.6), serine (R:0.8), threonine (R:0.7) and tryptophan (R:0.9);

μ is alanine (R:-1.8), methionine (R:-1.9) and tyrosine (R:-1.3);

π is arginine (R:4.5), asparagine (R:3.5), aspartic acid (R:3.5), glutamic acid (R:3.5), glutamine (R:3.5) and lysine (R:3.9); and ρ is alanine (R:-1.8), phenylalanine (R:-1.9) and tyrosine (R:-1.3).

Particularly preferred, however, is the retro-peptide of the sequence (SEQ ID NO:1):

$$NH_2-RKLAV-YWSSY-KRSRY-COOH$$

where the standard one-letter amino acid abbreviation is used.

However, it is explicitly contemplated that individual amino acids or clusters of 2 or 3 amino acids of the present amino acid sequences may be replaced with other non-naturally-occurring amino acids or structural homologues thereof or of naturally-occurring amino acids provided that on average the necessary R values are conserved.

In accordance with the present invention, the term "retro-peptide" means retro relative to the following antero-peptide sequence:

$$NH_2-YRSRK-YSSWY-VALKR-COOH$$

wherein Y is tyrosine, R is arginine, S is serine, K is lysine, W is tryptophan, V is valine and L is leucine, which is a portion of the basic FGF molecule entailing amino acids 106–120.

The effectiveness of the retro-peptides of the present invention is, indeed, quite surprising as they have no sequence homology with any known growth factor or receptor.

Hence, in one aspect of the present invention, the present retro-peptide may be advantageously used to block the FGF-receptor, thereby prohibiting or inhibiting entry of viruses into cells as the retro-peptide competes with the viruses for cellular attachment. This methodology is particularly effective against HSV-1 virion.

Additionally, it is known that tumors need blood supply for growth, and that growth of new blood vessels is induced by FGF released from tumor cells. If this pathway is blocked, tumors are unable to grow beyond about 2 mm in size. Hence, the present retro-peptide may be used not only to treat tumors directly, but also to prevent metastases.

Furthermore, the retro-peptide of the present invention may be used in the therapy of hypervascular disease and in re-stenosis of artery implants. It is known that several diseases are hypervascular in nature, such as diabetic retinopathy or psoriasis or rheumatoid arthritis or are induced by local hyperactivity of FGF. By blocking the FGF receptor, the progress of these diseases can be stopped or, at least, inhibited. Re-stenosis of artery implants, such as in coronary artery bypass, appears to be due to local action of FGF and, thus, appears preventable by using the present retro-peptide to block the FGF receptor.

The retro-peptide of the present invention may be synthesized using a standard solid-phase or liquid phase amino acid synthesis or may be provided by the fermentation of recombinant microorganisms. For example, the retro-peptide may be synthesized in accordance with U.S. Pat. Nos. 4,058,512 and 4,235,772 both of which are incorporated herein in the entirety. All of the retro-peptides of the present invention can be readily obtained by custom synthesis from a variety of commercially available chemical supply companies.

The retro-peptide may also, as indicated above, be prepared by the fermentation of transformed microorganisms containing a synthetic gene coding for the same. Conventional techniques may be used for the synthesis of the appropriate gene and for the transformation of a host microorganism. As a host microorganism, E. coli, for example, may be used. See, for example, Current Protocols in Molecular Biology (Wiley 1987).

In order to more fully explain the present invention, reference will now be made to FIGS. 1–5.

FIG. 1 illustrates the hydropathy pattern of the retro-peptide of the present invention. Upon inspection, symmetry may be seen with respect to the two hydrophobic ends and the neutral/hydrophilic middle part. This is the relevant primary structure required for activity.

Figure 2:
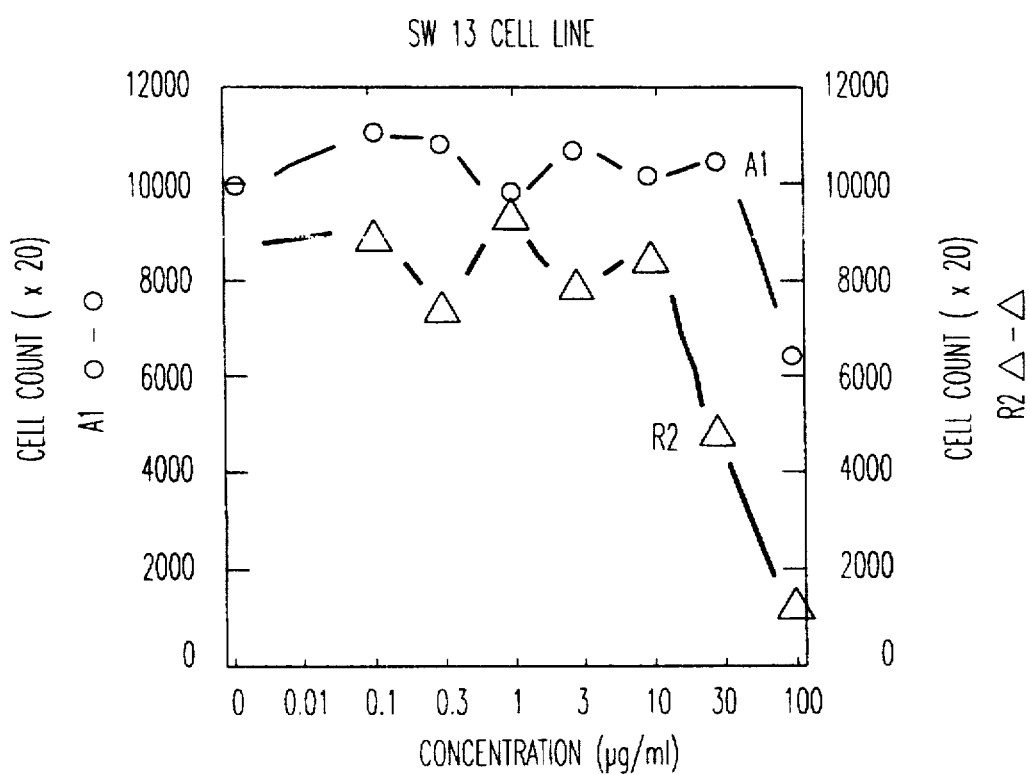
FIG. 2 illustrates the results of a growth assay conducted with both a peptide of the present invention (retro-peptide) and the antero-peptide sequence thereof.

FIG. 2 illustrates that both the antero-peptide and the retro-peptide are inhibitory in a growth assay with human SW-13 cells. Quite surprisingly, it is seen that the retro-peptide of the present invention is much more potent in this assay than the antero-peptide. Additionally, the retro-peptide is also observed to be effective at the same concentration against human melanoma, human rhabdomyosarcoma and also blocks FGF-stimulated growth of normal human cells.

In FIG. 2, "A" refers to the antero-peptide sequence, and "R" refers to the retro-peptide sequence.

Figure 3:
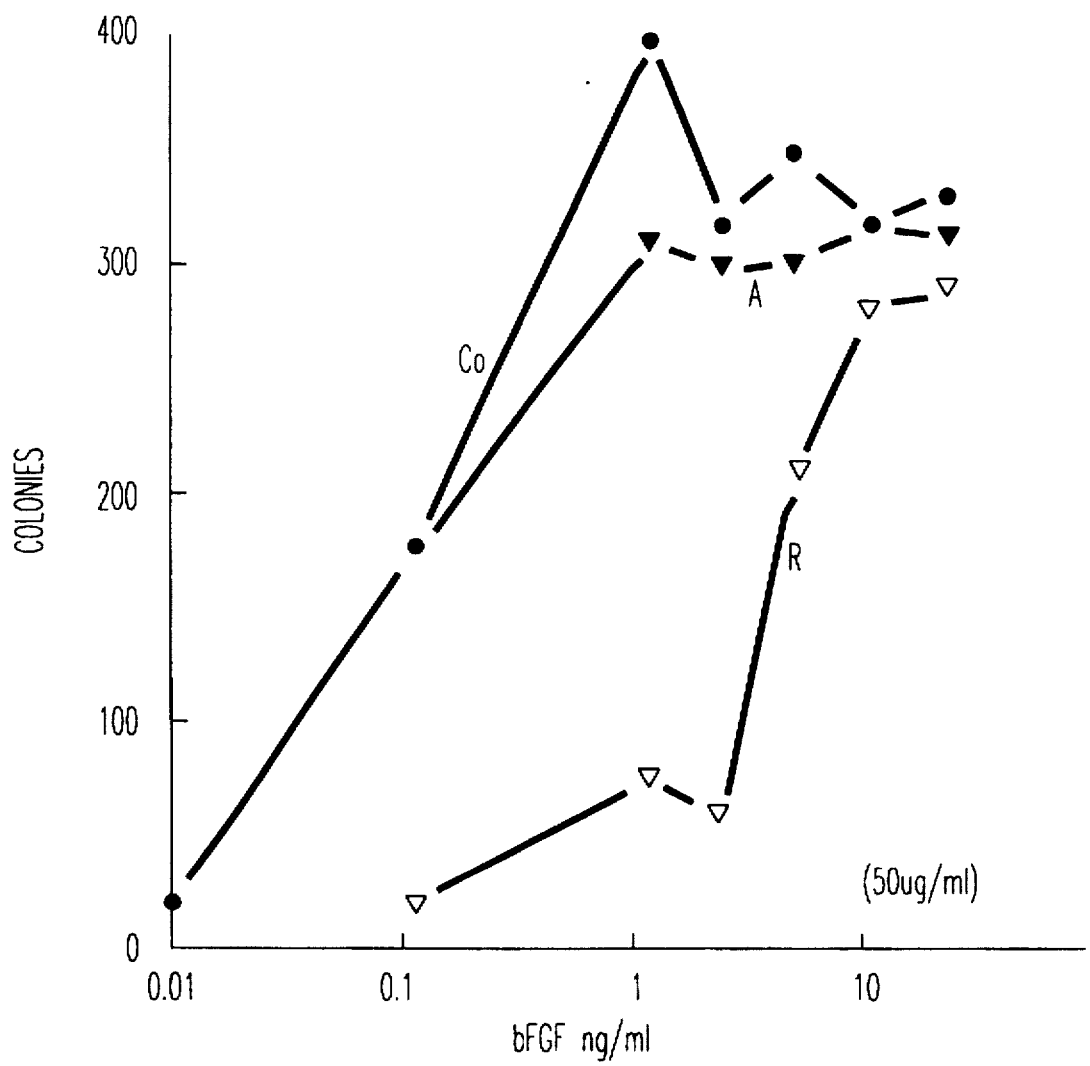
FIG. 3 illustrates the competitive mechanism of FGF-dependent growth inhibition by a retro-peptide of the present invention.

FIG. 3 illustrates the competitive mechanism of FGF-dependent growth inhibition by the retro-peptide of the present invention. A dose-response curve of FGF-stimulated colony formation of SW-13 cells is shifted to the right without affecting the maximum achieved. The antero-peptide is significantly less potent than the retro-peptide. Further, neither of the antero-peptide nor retro-peptide inhibit cell lines growing independently from FGF, such as breast cancer cells. This clearly establishes the specificity of the FGF-receptor inhibition by the present retro-peptide.

In FIG. 3, "Co" refers to a control, while "A" refers to the antero-peptide and "R" refers to the retro-peptide.

The importance of the two hydrophobic ends of the present retro-peptide is demonstrated by the effect of removing one hydrophobic end of the 15-mer retro-peptide. Notably, by removing one hydrophobic end of the 15-mer retro-peptide, a loss of activity is induced. This is clearly demonstrated in FIG. 4 where the activity of the 15-mer and of a 10-mer lacking the five amino acids are shown on SW-13 cells.

Figure 4:
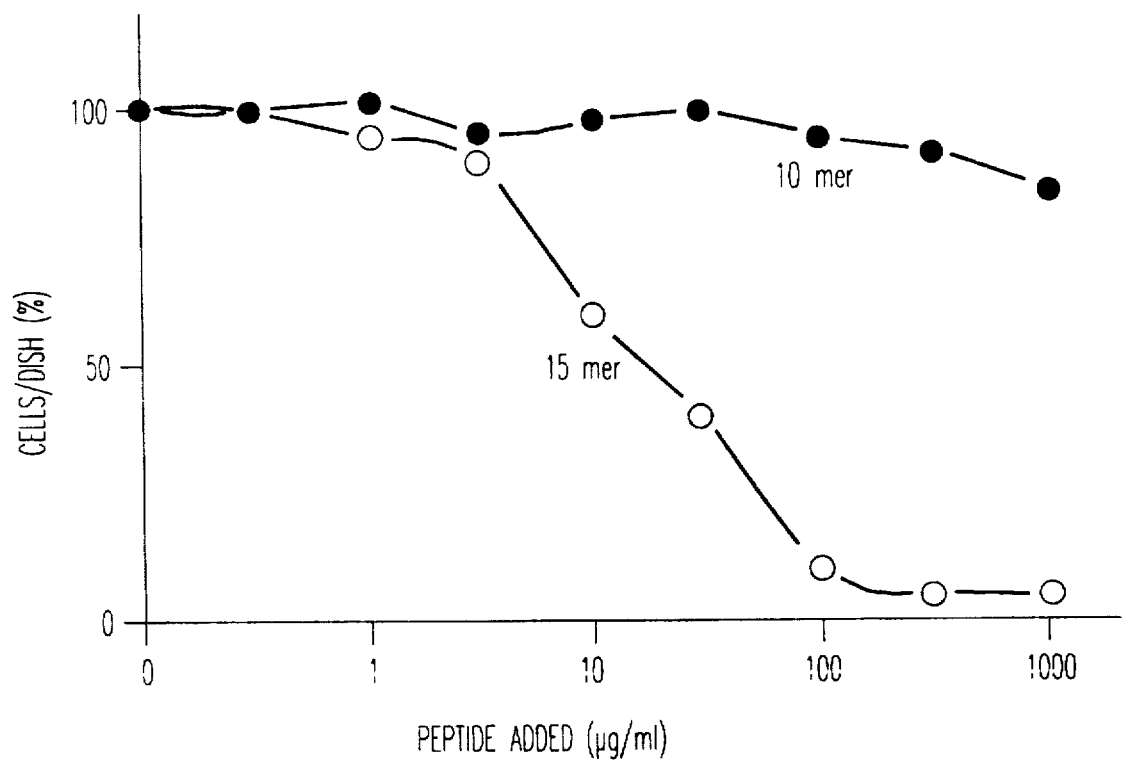
FIG. 4 illustrates a comparison of the effect of a 15 mer retro-peptide of the present invention and a C-terminally truncated 10-mer derivative of the 15-mer sequence.

FIG. 4 illustrates the difference in effect on SW-13 cell growth between a 10-mer peptide sequence of the formula (SEQ ID NO:6):

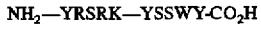

NH$_2$—YRSRK—YSSWY-CO$_2$H and a 15-mer peptide sequence of the formula (SEQ ID NO:1):

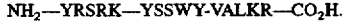

NH$_2$—YRSRK—YSSWY-VALKR—CO$_2$H.

As may be seen from FIG. 4, the 15-mer sequence has an inhibitive effect on SW-13 cell growth with increasing amount added in µg/ml. This effect becomes almost completely inhibiting in amounts added of about 100 µg/ml and greater. By contrast, the 10-mer sequence exhibits essentially no such inhibition even at amounts added of as high as 1,000 µg/ml.

The importance of utilizing a peptide sequence of at least 12 mer may be seen from FIG. 4. As already noted the present peptide sequences are from 12-mer to 30-mer.

In examining various peptide sequence homologies, it has been now noted that significant sequence homologies exist between the retro-peptide of the present invention (SEQ ID NO:2), and the Herpes Simplex virus UL21 protein (SEQ ID NO:3) and the Japanese encephalitis virus genome polyprotein (SEQ ID NO:4). This is illustrated in FIG. 5. That the present FGF-blocking peptide inhibits Herpes virus infectivity is clearly demonstrated by the structural homology with viral proteins.

Figure 6:
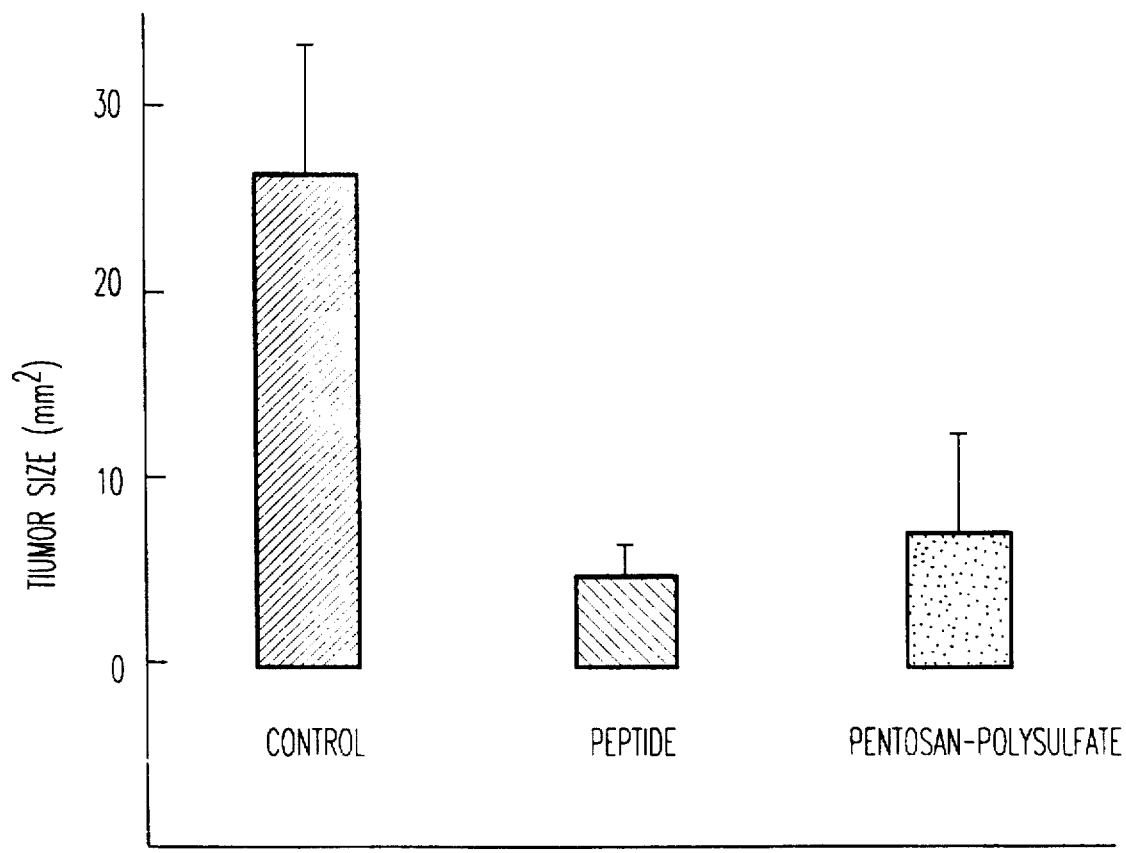
FIG. 6 illustrates the effect of the present peptides in treating human rhabdomyosarcoma.

Animal studies with human rhabdomyosarcoma growing in athymic nude mice were carried out with the 15 mer peptide. Tumors were allowed to grow subcutaneously and peptide (25 mg/kg of body weight) dissolved in saline was injected for eight days daily intraperitoneally. After three weeks the tumor size in a control group treated only with saline solution was 26.6±6.8 mm$^2$. The tumor size in the peptide-treated animals was 5.4±1.6 mm$^2$. These values are statistically significantly different as tested by the student's t-test (p<0.003). This is illustrated in FIG. 6.

The retro-peptide of the present invention may be administered by itself or as a component of a composition. Generally, whether administered by itself or as part of a composition, from about 10 µg to about 1,000 mg of retro-peptide per kg of mammalian body weight or compositions containing the same may be administered to any mammal in laboratory or veterinary practice, such as a mouse, cat, dog, cow or horse, however they are of particular use in humans.

In addition to the above range, lesser or greater amounts may be used as is required.

The present retro-peptide is water-soluble and is administered by any route, especially intravenously, subcutaneously, intraperitonially, intramuscularly, orally and rectally. The peptide may be conveniently administered in dextrose 5% saline or in saline solution.

The present peptide may also be microencapsulated in a lipid vesicle in accordance with a conventional encapsulation technique well known to those skilled in the art.

Additionally, in accordance with the present invention, it is advantageous if one or more of the present retro-peptides is formulated into a cream, lotion or solution for topical use on afflicted areas of the skin or easily accessible areas of the body surface such as the eyes or the genitalia. In preparing the cream, lotion or solution, any conventional and pharmaceutically acceptable base formulation may be used.

For example, a base formulation may be prepared in accordance with U.S. Pat. No. 4,849,425, with or without the antitumor active compounds described therein depending upon the intended use. Other antitumor active compounds may be included in the base formulation.

Additionally, a base formulation may be prepared in accordance with U.S. Pat. Nos. 4,760,096 or 4,126,702.

The above U.S. Patents are incorporated herein by reference in the entirety. However, these are only examples of known formulations which can be used.

Further, in addition to creams, lotions or solutions, the present peptides may be formulated as a type of lip balm which may be applied from a stick as a lipstick.

As noted above, the creams, lotions, solutions or lip balms are formulated such that about 10 μg to 1,000 mg of retropeptide can be dispensed per kg of mammalian body weight.

The present compositions may, as noted above, be used in the form of a solution which may be administered by intravenous or subcutaneous injection. Examples of liquid carriers are saline solution, dextrose 5% saline solution or water, all of which are suitable for injection.

When the above liquids are used for injection, particularly for humans, it is desirable, if not essential, that they be sterile so as to be suitable for injection.

In liquid compositions, the one or more peptides may, in general, comprise from about $10^{-7}$ g to $10^{-3}$ g/g of liquid carrier. The same concentrations apply for creams, lotions and lip balms.

Additionally, it is noted that the present peptide may be administered in conjunction with other ingredients in the composition, such as, for example, hormones and vitamins.

The present invention will now be further illustrated by reference to an example which is provided solely for illustration and is not intended to be limitative.

EXAMPLE

Human tumor cells (1 million per mouse) were inoculated in 0.1 ml of saline solution into a mammary fat pad of each mouse. Each group of treatment consisted of 10 animals. One day after the inoculation of tumor cells the animals were treated with a single daily intraperitoneal injection of saline solution (control group) or with the 15-mer retropeptide dissolved in saline solution at a dose of 25 mg per kg body weight (peptide group) or 25 mg per kg body weight of pentosanpolysulfate (pentosan polysulfate group). The treatment with peptide was continued for 8 days due to a currently still limited supply of the peptide. The pentosanpolysulfate treatment was continued throughout the whole observation period.

After about 2 weeks tumors became clearly visible in the control group (size of about 10 mm$^2$), but not in the peptide group. The mean ± standard error tumor size after 24 days of observation is shown in FIG. 6. The mean ± standard error tumor size is 26.6±6.8 mm$^2$ (control group) and 5.0±1.6 mm$^2$ (peptide group). This difference is highly significant ($p<0.003$) as tested by student's t-test. The animals tolerated the peptide well, and did not lose weight or show any other signs of major illness.

Pentosanpolysulfate was used as a control drug known by the present inventor's own studies to inhibit this tumor cell line. Its action is also significant ($p<0.05$).

FIG. 6 shows tumor size in mm$^2$ (length×width) of tumors growing subcutaneously in athymic nude mice.

From the above results, it is clear that the present peptides when injected (intraperitoneally in this case) are able to block subcutaneous growth of a human xenograft in mice. These peptides reach the circulatory system and tumors and are effective as an antitumor agent in animals.

In accordance with another aspect of the present invention, antibodies may be prepared against the present peptides using methodologies as described in U.S. Pat. Nos. 4,151,268, 4,197,237 and 4,123,431. Each and all of these patents are hereby incorporated in the entirety herein.

Further, monoclonal antibodies against the present peptides can be prepared using conventional methodologies. In turn, these monoclonal antibodies may be used to identify the present peptides to detect and quantify the present peptides, or even to purify the present peptides by immunoaffinity chromatography.

Additionally, in accordance with the present invention, antibodies may be used to attenuate the effect of the present peptide in a host. Also, the antibodies may be used to attenuate functions of proteins bearing the peptide sequence of interest.

Any number of techniques may be used, in accordance with the present invention, for rendering the present peptides immunogenic.

For example, the present peptides may be rendered immunogenic by conjugation with muramyl peptides as described in U.S. Pat. Nos. 4,639,512 and 4,461,761. Also, the present peptides may be rendered immunogenic by conjugation with other polypeptides as described in U.S. Pat. No. 4,812,554. Each of U.S. Pat. Nos. 4,639,512, 4,461,761 and 4,812,554 are incorporated herein in the entirety.

By raising either monoclonal or polyclonal antibodies to the present peptides, an assay procedure can be used for the present peptides.

In addition to the peptides and pharmaceutical compositions containing the same as described above, the present invention also provides both monoclonal and polyclonal antibodies against the present peptides. The present invention also provides a method of using the antibodies for therapeutic purposes. Further, the present invention also provides a diagnostic test kit.

Any of the peptides of the present invention individually or in combination, can be used to prepare monoclonal or polyclonal antibodies using known procedures as described in the above-identified U.S. patents incorporated herein in the entirety. These antibodies may, in turn, be used diagnostically and therapeutically to detect the present peptides.

In more detail, the monoclonal and/or polyclonal antibodies of the present invention may be used to therapeutically detect and monitor the amount of any of the present peptides in mammalian serum. Generally, any suitable means of detection may be used. However, it is preferred that a two-site immunoassay be used. A two-site, two-step immunoradiometric procedure is generally described in U.S. Pat. No. 4,353,982, which is incorporated herein in the entirety.

In such a technique, an insoluble support is provided having a primary antibody attached thereto. The primary antibody may be bonded to the insoluble support by conventional processes.

The insoluble support having a primary antibody attached thereto is contacted with mixture containing serum sample in an aqueous dilution buffer for a time adequate to permit conjugation of the primary antibody with the peptide analyte.

The insoluble support is then separated from the primary reaction mixture.

Then, the insoluble support is contacted with an aqueous conjugate dilution buffer solution containing a secondary antibody which binds selectively with the peptide analyte for a time adequate to permit conjugation of the secondary antibody to the peptide analyte. The secondary antibody is coupled to a label. But for the label, however, the secondary antibody is preferably the same as the first antibody.

Thereafter, the label attached to the insoluble support is detected and the amount of peptide analyte present is determined. The label may be a physically detectable label such as a radiolabel, fluorophore or chromophore or an enzyme, which is subsequently reacted with a substrate which yields a physically detectable reaction product.

As noted above, primary antibody can be bonded to the insoluble support by conventional processes. Procedures for binding of antibodies to insoluble supports are described in U.S. Pat. Nos. 3,551,555, 3,553,310, 4,048,298 and RE-29, 474, for example, all of which are incorporated herein in the entirety. Binding of antibodies to polystyrene by adsorption has been described in U.S. Pat. Nos. 3,646,346 and 4,092,408, for example.

A variety of materials can be used as the insoluble support, the most important factor being the binding of the primary antibody to the surface, the absence of interference with the conjugation reactions or with other reactions which can be employed to determine the presence and extent of the conjugating reaction. Organic and inorganic polymers, both natural and synthetic, can be used as the insoluble support. Examples of suitable polymers include polyethylene, polypropylene, polybutylene, poly(4-methylbutylene), butyl rubber, silastic polymers, polyesters, polyamides, cellulose and cellulose derivatives, such as cellulose acetate, nitrocellulose and the like, acrylates, methacrylates, vinyl polymers, such as polyvinyl acetate, polyvinyl chloride, polyvinylidene chloride, polyvinyl fluoride, and the like, polystyrene and styrene graft copolymers, rayon, nylon, polyvinylbutyrate, polyformaldehyde, for example. Other materials which can be used as the insoluble support can be the latexes of the above polymers, silica gel, silicon wafers, glass, paper, insoluble protein, metals, metalloids, metal oxides, magnetic materials, semi-conductive materials, cermets and the like. Further, substances which form gels, for example proteins such as gelatins, lipopolysaccharides, silicates, agarose, polyacrylamides or polymers which form several aqueous phases such as dextrans, polyalkylene glycols (alkylene with 2 to 3 carbon atoms) or surfactants, e.g. amphophilicompounds such as phospholipids, long chain (12–24 carbon atoms) alkyl ammonium salts and the like may also be used.

A preferred diagnostic support entails a polystyrene or styrene copolymers such as styrene-acrylonitrile copolymers, or polyolefins such as polyethylene or polypropylene, and acrylate and methacrylate polymers and copolymers. The primary antibody can be coordinated or bound to the insoluble support by adsorption, ionic bonding, van der Waals adsorption, electrostatic bonding, or other non-covalent bonding, or it can be bound to the insoluble support by covalent bonding. Preferred forms of insoluble supports are beads, microwells and dipsticks.

The aqueous dilution buffer may be a conventional buffer such as one containing a phosphate buffer, pH base 7.5 having a 0.1% sodium azide preservative. Such a buffer is described in U.S. Pat. No. 4,267,271, which is incorporated herein in the entirety. Additionally, the buffer may also contain a sulfhydryl group protecting agent such as is described in U.S. Pat. No. 4,267,271, which is incorporated herein in the entirety.

Generally, the buffer solution contains one or more buffering agents which are compatible with the other components of the solution and with the sulfhydryl group protecting agent, such as mercaptoethanol. Examples of buffers which are suitable for use with sulfhydryl group stability agents are tromethamine (Tris), triethanolamine, imidazole acetate, imidazole and bis-(2-hydroxyethyl)-imino-tris-(hydroxymethyl)methane (bis-Tris), for example. Generally, the buffer solution has a molar concentration of from 0.01 to 0.5M and preferably from 0.05 to 0.2M. In general, the buffer solution has a pH of from 6 to 9, preferably from 7 to 8.5.

The sample dilution buffer solution preferably contains a multivalent cation inhibiting amount of chelating agent. The amount depends upon the choice of chelating agent. Suitable chelating agents include ethylenediamine tetracetic acid and the alkali metal and ammonium salts thereof (EDTA). When the chelating agent is EDTA, the preferred amounts in the solution is within the range of from 0.01 to 0.1 (w/v) %.

The sample dilution buffer solution also preferably contains an antimicrobial agent such as sodium azide and the like which does not interfere with the immunochemical reactions. The preferred concentrations of sodium azide in the solution are from 0.017 to 0. 3 wt. %.

The sample dilution buffer solution also preferably contains a quantity of accelerating agent sufficient to increase the analyte with primary antibody conjugation rate. Preferred accelerating agents are polyethylene glycols having molecular weights within the range of from 1000 to 8000 and optimally from 7000 to 8000. The accelerating agent concentration is preferably within the range of from 0 up to 2 wt. % in the solution.

The incubation between the primary antibody and sample is continued until substantial conjugation of the primary antibody with the analyte, if any is present, can occur. The time is dependent upon the size of the analyte and the temperature of the solution. Suitable incubation times are from about 2 to 240 minutes at temperatures within the range of from 15° to 45° C., the preferred incubation or contact time being within the range of from 5 to 45 minutes at the preferred temperatures within the range of from 18° to 30° C.

The aqueous dilution buffer solution is then rinsed from the insoluble support. Suitable rinse solutions are buffered solutions which do not leave a residue which will interfere with the second incubation step in the method of this invention. Conventional buffer solutions such as buffered salines, phosphate buffer solutions and borate buffer solutions can be used. A preferred rinse buffer solution is a phosphate buffer solution having a phosphate molarity of from 0.02 to 0.2M and a pH of from 7 to 8.7.

In the second step, the insoluble support is contacted with an aqueous conjugate dilution buffer solution containing a secondary antibody which binds selectively with the analyte for a time sufficient to permit secondary antibody conjugation with analyte. The antibody is coupled with a label, but is otherwise preferably the same as the primary antibody.

The aqueous conjugate dilution buffer solution can contain agents which reduce non-specific binding, accelerate the secondary conjugation reaction, and inhibit microbial growth. The buffering agents in the aqueous conjugate dilution buffer solution can be any conventional buffering agents which provide the desired pH range and do not interfere with the secondary conjugation reaction. Conventional buffer solutions such as buffered salines, phosphate buffer solutions and borate buffer solutions can be used. A preferred rinse buffer solution is a phosphate buffer solution having a phosphate molarity of from 0.02 to 0.2M and a pH of from 7 to 8.7.

The aqueous conjugate dilution buffer solution is mixed with the secondary antibody for use in the second step of the immunoassay. While the secondary antibody is preferably the same as the primary antibody, the secondary antibody can be any monoclonal antibody, mixture of monoclonal antibodies, polyclonal antibodies or mixtures thereof which bind selectively with the analyte being determined in the assay. These antibodies are preferably coupled to a label. However, any physically detectable label or moiety which can be further treated to yield a physically detectable label can be used as the label.

The labels can be coupled with the secondary antibody by conventional procedures for attaching labels to proteins. The labels can be bonded or coupled to the protein reagents by chemical or physical bonding. Ligands and groups which can be conjugated to the secondary antibodies of this invention include elements, compounds or biological materials which have physical or chemical characteristics which can be used to distinguish the reagents to which they are bonded from compounds and materials in the sample being tested. A wide variety of such labels and methods for coupling them to antibodies are well-known and conventional in the art.

Radiolabeled secondary antibodies can be used in the method of this invention. The specific activity of a tagged antibody depends upon the half-life, isotopic purity of the radioactive label and how the label is incorporated into the antibody. Table I lists several commonly used isotopes, their specific activities and half-lives. In immunoassay tests, the higher the specific activity, in general, the better the sensitivity.

TABLE I

| Isotope | Specific Activity of Pure Isotope (Curies/mole) | Half-Life |
|---------|--------------------------------------------------|-----------|
| $14_C$  | $6.25 \times 10^1$ | 5720 years |
| $3_H$   | $2.91 \times 10^4$ | 12.5 years |
| $35_S$  | $1.50 \times 10^6$ | 87 days |
| $125_I$ | $2.18 \times 10^6$ | 60 days |
| $32_P$  | $3.16 \times 10^6$ | 14.3 days |
| $131_I$ | $1.62 \times 10^7$ | 8.1 days |

The antibodies of the present invention may be labeled with radioisotopes using conventional and well known processes. For example, U.S. Pat. No. 4,302,438 describes tritium labeling procedures, and is incorporated herein in the entirety. Also, U.S. Pat. Nos. 3,867,517 and 4,376,110 describe procedures for iodinating antibodies, and are both incorporated herein in the entirety.

Antibodies labeled with enzymes are particularly useful in the method of this invention. Examples of suitable systems, coupling procedures and substrate reactions therewith are disclosed in U.S. Pat. Nos. 31,006, 4,214,048, 4,289,747, 4,302,438, 4,312,943, 4,376,110 and the references cited therein, for example. Each of these patents are incorporated herein in the entirety. Examples of other suitable systems are described by Pesce et al, Clin. Chem. 20(3):353–359 (1974) and Wisdom, G., Clin. Chem. 22:1243 (1976).

A list of suitable enzyme classes and specific examples therefor are recited hereinbelow in Table II:

TABLE II

| Class | Enzyme Example |
|-------|----------------|
| Hydrolases Carbohydroases | Anylases |
| Nucleases | Polynucleotidase |
| Amidases | Arginase |
| Purine deaminases | Adenase |
| Peptidases | Aminopolypeptidase |
| Proteinases | Pepsin |
| Esterases | Lipases |
| Iron Enzymes | Catalase |
| Copper Enzymes | Tyrosinases |
| Enzymes containing Coenzymes | Alcohol dehydrogenase |
| Enzymes reducing cytochrome | Succinic dehydrogenase |
| Yellow enzymes | Diaphorase |
| Mutases | Glyoxalase |
| Demolases | Aldolase |
| Oxidases | Glucose oxidase |
|  | Horse radish peroxidase |
| Phosphatases | Alkaline phosphatase |
| Other enzymes | β-galactosidase |
|  | Phosphorylases |
|  | Hexokinases |

A list of suitable enzymes are described in Hawk, et al. PRACTICAL PHYSIOLOGICAL CHEMISTRY, New York: McGraw-Hill pp. 306–397 (1954).

Fluorogenic enzymes (enzymes in the presence of which a selected substrate will produce a fluorescent product) are useful labeling moieties. Methods for selectively conjugating enzymes to antibodies without impairing the ability of the antibody to bind with antigen are well known in the art. Suitable enzymes and procedures for coupling them to antibodies are described by Wilson, M. et al. Recent developments in the periodate method for conjugating horseradish peroxidase (HRPO) to antibodies. INTERNATIONAL CONFERENCE IN IMMUNOFLUORESCENCE AND RELATED STAINING TECHNIQUES. W. Knapp et al, editors. Amsterdam: Elsevier pp. 215–244 (1978), Sullivan, M. et al. Enzyme immunoassay: a review. Annals of Clinical Biochemistry. 16:221–240 (1979) and in U.S. Pat. No. 4,190,496, for example. The preferred fluorogenic enzymes and suitable substrates corresponding thereto include horseradish peroxidase for which a suitable substrate is homovanillic acid or 4-hydroxy-3-methoxy-phenylacetic acid, 8-galactosidase for which a suitable substrate is 4-methylumbelliferyl-β-D-galactoside, alkaline phosphatase for which a suitable substrate is 4-methylumbelliferyl phosphate and other umbelliferyl phosphates such as 4-carboxyumbelliferyl phosphate and umbelliferyl phosphate 4-carboxyalkyl-esters, etc.

Fluorescent labeled antibodies can be prepared from standard fluorescent moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescers are described by Stryer, Science. 162:526 (1968)

and Brand, L. et al, "Fluorescent probes for structure," Annual Review of Biochemistry. 41:843–868 (1972). The antibodies can be labeled with fluorescent groups by conventional procedures such as those disclosed in U.S. Pat. Nos. 3,940,475, 4,289,747 and 4,376,110, for example, which are each incorporated herein in the entirety.

The aqueous conjugate dilution buffer solution can contain from 0.5 to 10 wt. % polyethylene glycol and optimally contains from 1 to 5 wt. % polyethylene glycol. The polyethylene glycol can have a molecular weight within the range from 1,000 to 8,000 and preferably within the range from 2,000 to 4,000. This reagent accelerates the rate of secondary conjugation. Excess amounts of polyethylene glycol may cause a precipitation of protein or flatten the response curve.

The conjugate dilution buffer solution can contain a non-specific binding inhibiting amount of a conventional non-immune serum or other water-soluble animal protein or water-soluble amino acid polymer. It preferably contains from 3 to 10 (v/v) % of non-immune protein or from 3 to 10 wt. % of the animal protein or amino acid polymer. Examples of suitable conventional and well-known non-immune serums include bovine serum albumins (BSA), human (HSA), rabbit (RSA), goat (GSA), sheep (SHA), horse (HOSA), etc.; serum gamma globulin, of the previously described animals and other animal proteins such as ovalbumin, fibrinogen, thrombin, transferrin, glycoproteins, etc. Examples of water-soluble amino acid polymers include polylysine, polyglutamic acid, polyalanine, polyhistidine, polymethionine, polyproline, etc.

The conjugation dilution buffer solution also preferably contains an amount of antimicrobial agent sufficient to inhibit microbial growth in the solution. The solution preferably contains from 0.01 to 0.2 wt. % of antimicrobial agent such as sodium ethylmercuric thiosalicylate or one or more of other antimicrobial agents which do not interfere with the secondary conjugation reaction.

The incubation between the secondary antibody and the insoluble support is continued until substantial conjugation of the secondary antibody with the analyte, if any, present on the insoluble support can occur. The time is dependent upon the temperature of the solution. Suitable incubation times are from about 2 to 240 minutes at temperatures within the range of from 15° to 45° C., the preferred incubation or contact time being within the range of from 5 to 45 minutes at the preferred temperatures within the range of from 18° to 30° C.

The insoluble support is then rinsed to remove residual conjugate dilution buffer solution. The rinse solution should be free of any materials which would interfere with the subsequent label determination procedure. The rinse solution described above is suitable.

The label adhering to the insoluble support is then determined. If the label is a physically detectable moiety such as a radiolabel, chromophore or fluorophore, for example, it can be measured directly using suitable, conventional methods and devices.

If the secondary antibody label is an enzyme, the enzyme adhering to the insoluble support is determined by reacting it with a substrate which undergoes a chemical reaction in the presence of the enzyme to yield a physically detectable reaction product. The physically detectable reaction product produced by the reaction is then determined.

The present invention also provides a test kit which may be used diagnostically in the detection of the above-disclosed peptides. In essence, the test kit may be used to detect the presence of the peptides or may also be used to determine the amount of peptide present to ascertain whether additional peptide must be administered.

Generally, the test kit of the present invention is for the detection of receptor blocking peptides of fibroblast growth factor receptor. Further, it is preferred that a two-site, two-step assay be conducted.

Generally, a mobile particulate solid phase having bound polyclonal or monoclonal antibodies thereto against the present peptides is contacted with mammalian serum, particularly human serum.

Then, the solid-phase portion of each is removed and contacted with a tracer solution including a labelled second antibody which allows for the detection of the presence of peptide.

For example, by using the antibodies of the present invention, a test kit may be constructed analogous to that disclosed in U.S. Pat. No. 4,624,916, which is incorporated herein in the entirety.

In more detail, the present test kit is for the detection of FGF receptor blocking peptides and contains:

1) a solid-phase matrix containing an insoluble support having attached thereto a primary antibody against a peptide of interest, and having a liquid phase surrounding the solid-phase matrix;

2) a series of calibrating liquids each liquid containing a different known amount of FGF receptor blocking peptide;

3) a wash buffer; and 4) a tracer solution containing a labeled secondary antibody against with the peptide of interest.

Typically, five differing calibrations are included to provide an accurate calibration curve against the serum samples tested. However, as few as two differing calibrations or more than five of the same may be used.

In accordance with the present invention, both the primary and secondary antibodies are raised against the peptide analyte, and are preferably the same but for the detectability of the second antibody.

Having described the present invention, it will be apparent to one skilled in the art that many changes and modifications can be made to the embodiments described above without departing from the spirit and the scope of the present invention.

What is claimed as new and desired to be secured by Letters Patent of the United States is:

1. A peptide which blocks Fibroblast Growth Factor (FGF)-receptor, having the formula (SEQ ID NO:5):

$H_2N$—RKLAV—YWSSY—KRSRY—COOH wherein:

R is arginine, K is lysine, L is leucine, A is alanine, V is valine, Y is tyrosine, W is tryptophan and S is serine.

2. A pharmaceutical composition which blocks FGF-receptor, which comprises an effective amount of the peptide of claim 1, and a pharmaceutically acceptable carrier.

3. The pharmaceutical composition of claim 2, which is in a form for topical administration.

4. The pharmaceutical composition of claim 3, wherein said form is a cream, lotion, solution or lip balm.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( x ) PUBLICATION INFORMATION:
    ( A ) AUTHORS: Baird, A. et al
    ( C ) JOURNAL: Proc. Natl. Acad. Sci. U.S.A.
    ( D ) VOLUME: 85
    ( F ) PAGES: 2324-2328
    ( G ) DATE: 1988

( x i ) SEQUENCE DESCRIPTION: SEQ ID NO:1:

```
Tyr Arg Ser Arg Lys Tyr Ser Ser Trp Tyr Val Ala Leu Lys Arg
1               5                   10                  15
```

( 2 ) INFORMATION FOR SEQ ID NO:2:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( v i ) ORIGINAL SOURCE:
    ( A ) ORGANISM: Herpes simplex virus
    ( B ) STRAIN: HFEM ( x i ) SEQUENCE DESCRIPTION: SEQ ID NO:2:

```
Gln Lys Leu Ala Val Tyr Tyr Tyr Ile Ile His Arg Glu Arg Arg
1               5                   10                  15
```

( 2 ) INFORMATION FOR SEQ ID NO:3:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( v i ) ORIGINAL SOURCE:
    ( A ) ORGANISM: Herpes simplex virus
    ( B ) STRAIN: 17

( x i ) SEQUENCE DESCRIPTION: SEQ ID NO:3:

```
Gln Lys Leu Ala Val Tyr Tyr Tyr Ile Ile His Arg Glu Arg Arg
1               5                   10                  15
```

( 2 ) INFORMATION FOR SEQ ID NO:4:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( v i ) ORIGINAL SOURCE:
    ( A ) ORGANISM: Japanese encephalitis virus
    ( B ) STRAIN: wild type ( x i ) SEQUENCE DESCRIPTION: SEQ ID NO:4:

```
Gly Lys Leu Thr Pro Tyr Trp Gly Ser Val Lys Glu Asp Arg Ile
1               5                   10                  15
```

( 2 ) INFORMATION FOR SEQ ID NO:5:

( i ) SEQUENCE CHARACTERISTICS:

```
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

Arg  Lys  Leu  Ala  Val  Tyr  Trp  Ser  Ser  Tyr  Lys  Arg  Ser  Arg  Tyr
     1              5                            10                         15

( 2 ) INFORMATION FOR SEQ ID NO:6:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

Tyr  Arg  Ser  Arg  Lys  Tyr  Ser  Ser  Trp  Tyr
     1              5                           10
```